(12) United States Patent
Antwiler

(10) Patent No.: US 8,321,145 B2
(45) Date of Patent: Nov. 27, 2012

(54) PREDICTOR OF WHEN TO HARVEST CELLS GROWN IN A BIOREACTOR

(75) Inventor: Glen Delbert Antwiler, Lakewood, CO (US)

(73) Assignee: Terumo BCT, Inc., Lakewood, CO (US)

( * ) Notice: Subject to any disclaimer, the term of this patent is extended or adjusted under 35 U.S.C. 154(b) by 471 days.

(21) Appl. No.: 12/536,707

(22) Filed: Aug. 6, 2009

(65) Prior Publication Data

US 2010/0042260 A1 Feb. 18, 2010

Related U.S. Application Data

(60) Provisional application No. 61/088,223, filed on Aug. 12, 2008, provisional application No. 61/160,082, filed on Mar. 13, 2009.

(51) Int. Cl.
*G01N 33/50* (2006.01)
*G01N 33/48* (2006.01)

(52) U.S. Cl. ............................................ 702/19; 702/20

(58) Field of Classification Search ........................ None
See application file for complete search history.

(56) References Cited

U.S. PATENT DOCUMENTS

| | | | |
|---|---|---|---|
| 5,126,238 | A | 6/1992 | Gebhard et al. |
| 5,202,254 | A | 4/1993 | Amiot et al. |
| 5,656,421 | A | 8/1997 | Gebhard et al. |
| 6,077,708 | A | 6/2000 | Collins et al. |
| 7,041,493 | B2 | 5/2006 | Rao |
| 2009/0104653 | A1* | 4/2009 | Paldus et al. ................. 435/39 |
| 2009/0269841 | A1 | 10/2009 | Wojciechowski et al. |

FOREIGN PATENT DOCUMENTS

JP 3047074 2/1991

OTHER PUBLICATIONS

Clausen et al. ("Lactate as an indicator of terminating time in insect cell culture baculoviruns expression vector systems" Biotechnology Techniques, vol. 10, No. 10, Oct. 19996, pp. 1-5.*
Biovest International, "AutovaxID: advanced hollow fibre bioreactors with automated lactate control yield higher density monoclonal antibody production", *VWRbioMarke*, No. 21, Sep. 2008, pp. 10-11.
Grayson et al, "Effects of Hypoxia on Human Mesenchymal stem Cell Expansion and Plasticity in 3D Constructs", *J. Cellular Physiology*, 2006, 207:331-339.
Wang et al, "Influence of Oxygen on the Proliferation and Metabolism of Adipose Derived Adult Stem Cells", *J. Cellular Physiology*, 2005, 204:184-161.
Zhao et al, "Effects of Oxygen Transport on 3-D human Mesenchymal Stein Cell Metabolic Activity in Perfusion and Static Cultures: Experiments and Mathematical Model", *Biotechnol. Prog*, 2005, 27, 1269-1280.
Zhao et al, "Perfusion Bioreactor System for Human Mesenchymal Stem Cell Tissue Engineering: Dynamic Cell Seeding and Construct Development", *Biotechnology and Bioengineering*, vol. 91, No. 4, Aug. 20, 2005, pp. 482-493.
PCT/US2009/052970, filed Aug. 8, 2009, "International Search", mailed Jul. 7, 2010.
Clausen et al, "Lactate as an Indicator of Terminating Time in Insect Cell Culture Baculoviruns Expression Vector Systems", *Biotechnology Techniques*, vol. 10, No. 10, Oct. 1996, pp. 721-726.
Ozturk et al, "Real-Time Monitoring and Control of Glucose and Lactate Concentrations in a Mammalian Cell Perfusion Reactor", *Biotechnology and Bioengineering*, vol. 53, No. 4, Feb. 1997, pp. 372-378.

* cited by examiner

*Primary Examiner* — Jason Sims
(74) *Attorney, Agent, or Firm* — Elizabeth J. Reagan; John R. Merkling; René A. Pereyra

(57) ABSTRACT

This invention relates to a cell expansion system and to a method of determining when to harvest cells from the cell expansion system.

14 Claims, 5 Drawing Sheets

PREDICTOR OF WHEN TO HARVEST CELLS GROWN IN A BIOREACTOR

CROSS REFERENCE TO RELATED APPLICATIONS

This application claims the benefit of U.S. Provisional Application No. 61/088,223 filed Aug. 12, 2008 and U.S. Provisional Application No. 61/160,082 filed Mar. 13, 2009.

BACKGROUND

Human stem cells, which have been expanded in culture from a small amount of donor cells, can be used to repair or replace damaged or defective tissues and have broad clinical applications for treatment of a wide range of diseases. Recent advances in the area of regenerative medicine demonstrate that stem cells have unique properties such as self-renewal capacity, the ability to maintain the unspecialized state, and the ability to differentiate into specialized cells under particular conditions.

As an important component of regenerative medicine, the bioreactor or cell expansion system plays a role in providing optimized environments for cell growth and expansion. The bioreactor provides nutrients to the cells and removal of metabolites, as well as furnishing a physiochemical environment conducive to cell growth in a closed, sterile system. Cell expansion systems can be used to grow other types of cells as well as stem cells.

Many types of bioreactors are currently available. Two of the most common include flat plate bioreactors and hollow fiber bioreactors. Flat plate bioreactors enable cells to grow on large flat surfaces, while hollow fiber bioreactors enable cells to grow either on the inside or outside of the hollow fibers.

It is not current practice to look inside a bioreactor to determine when to harvest the expanded cells without destroying the sterility of the closed system. A way to determine when to harvest the cells while still maintaining sterility is necessary. It is to such methods that the present invention is directed.

SUMMARY OF THE INVENTION

The invention relates to a method of determining when to harvest cells from a cell growth chamber of a cell expansion system. The steps include measuring the number of cells initially loaded into the cell growth chamber; measuring the concentration of lactate generated at various times throughout a cell expansion cycle; and using the measurements to determine when to harvest the expanded cells from the cell growth chamber at the end of a cell expansion cycle.

The invention also relates to a cell expansion system which includes a cell growth chamber containing cells; at least one pump and a digital computer. The digital computer further includes at least one processor; a memory; a user interface; and a controller interface. The user interface is configured to allow an operator to enter the number of cells initially loaded into the cell growth chamber and the concentration of lactate measured at various times during a cell expansion cycle. The memory takes the number of cells initially loaded into the cell growth chamber and the concentration of lactate measured at various times throughout the cell expansion cycle to determine when the cells in the cell growth chamber should be harvested. The memory then sends a signal through the processor to the controller interface to instruct the at least one pump to pump fluid through the cell growth chamber to remove the cells from the cell growth chamber.

DETAILED DESCRIPTION

As discussed above, a number of bioreactor or cell growth chamber configurations exist for culturing cells. No particular configuration is required for this invention. However, as but one example, not meant to be limiting, is a hollow fiber bioreactor shown in FIG. 1.

Figure 1:
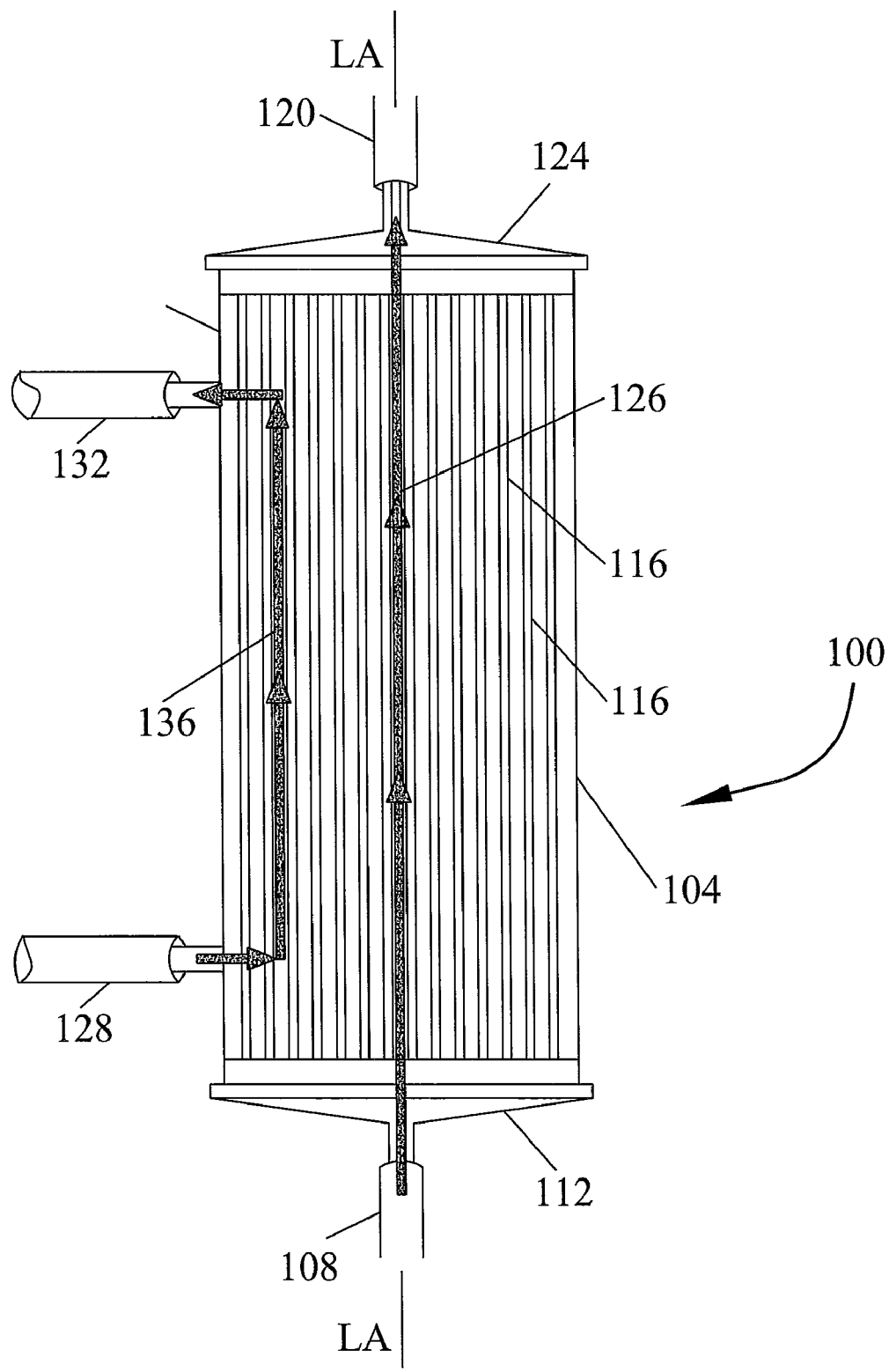
FIG. 1 is a front side elevation view of an embodiment of a cell growth chamber.

With reference now to FIG. 1, an example of a cell growth chamber 100 is shown in front side elevation view. Cell growth chamber 100 has a longitudinal axis LA-LA and includes cell growth chamber housing 104. In at least one embodiment, cell growth chamber housing 104 includes four openings or ports: IC inlet port 108, IC outlet port 120, EC inlet port 128, and EC outlet port 132.

Fluid in a first circulation path enters cell growth chamber 100 through IC inlet port 108 at a first longitudinal end 112 of the cell growth chamber 100, passes into and through the intracapillary side (referred to in various embodiments as the intracapillary ("IC") side or "IC space" of a hollow fiber membrane) of a plurality of hollow fibers 116 (the hollow fibers are also generally referred to as a membrane), and out of cell growth chamber 100 through IC outlet port 120 located at a second longitudinal end 124 of the cell growth chamber 100. The fluid path between the IC inlet port 108 and the IC outlet port 120 defines the IC portion 126 of the cell growth chamber 100. Fluid in a second circulation path flows in the cell growth chamber 100 through EC inlet port 128, comes in contact with the extracapillary side or outside (referred to as the "EC side" or "EC space" of the membrane) of the hollow fibers 116, and exits cell growth chamber 100 via EC outlet port 132. The fluid path between the EC inlet port 128 and the EC outlet port 132 comprises the EC portion 136 of the cell growth chamber 100. Fluid entering cell growth chamber via the EC inlet port 128 is in contact with the outside of the hollow fibers 116. Small molecules (e.g., water, oxygen, lactate, etc.) can diffuse through the hollow fibers from the interior or IC space of the hollow fibers to the EC space, or from the EC space to the IC space. Large molecular weight molecules such as growth factors are typically too large to pass through the hollow fiber membrane, and remain in the IC space of the hollow fibers. The media may be replaced as needed. Media may also be circulated through an oxygenator to exchange gasses as needed. Cells can be contained within the first circulation path and/or second circulation path, and can be on either the IC side and/or EC side of the membrane.

Although cell growth chamber housing 104 is depicted as cylindrical in shape, it could have a variety of shapes, such as a rectangular cube. Cell growth chamber housing 104 can be made of any type of biocompatible polymeric material.

Figure 2:
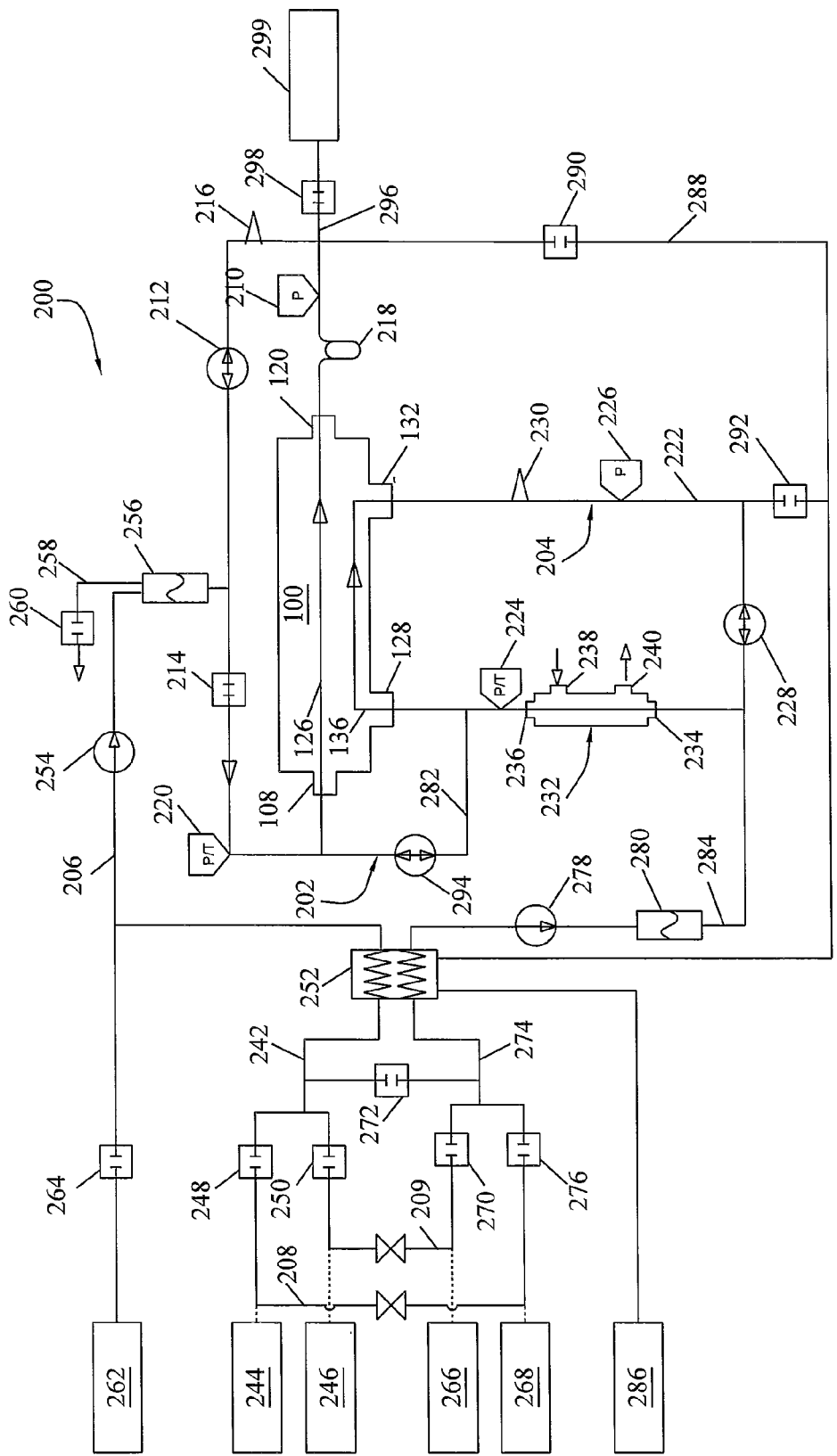
FIG. 2 is a schematic of an embodiment of a cell expansion system.

Referring now to FIG. 2, a schematic of one possible embodiment of a cell expansion system (CES) is shown. CES 200 includes first fluid circulation path 202 (also referred to as the "intracapillary loop" or "IC loop") and second fluid circulation path 204 (also referred to as the "extracapillary loop" or "EC loop"). First fluid flow path 206 is fluidly associated with cell growth chamber 100 to form first fluid circulation path 202. Fluid flows into cell growth chamber 100 through IC inlet port 108, through hollow fibers in cell growth chamber 100, and exits via IC outlet port 120. Pressure gauge 210 measures the pressure of media leaving cell growth chamber 100. Media flows through IC circulation pump 212 which can be used to control the rate of media flow. Media then flows through valve 214. As those skilled in the art will appreciate, additional valves and/or other devices can be placed at various locations to isolate and/or measure characteristics of the media along portions of the fluid paths. Accordingly, it is to be understood that the schematic shown represents one possible configuration for various elements of the CES and modifications to the schematic shown are within the scope of the one or more present inventions.

With regard to the IC loop, samples of media can be obtained from sample port 216 or sample coil 218 during operation. Pressure/temperature gauge 220 disposed in first fluid circulation path 202 allows detection of media pressure and temperature during operation. A biosensor (not shown) may also be fluidly disposed in first 202 fluid circulation path to allow for the measurement of metabolite levels within the fluid flow paths. Media then returns to IC inlet port 108 to complete fluid circulation path 202. Cells grown/expanded in cell growth chamber 100 can be flushed out of cell growth chamber 100 via line 296 and valve 298 or redistributed within hollow fibers for further growth.

Second fluid circulation path 204 includes second fluid flow path 222 that is fluidly associated with cell growth chamber 100 in a loop. Fluid in second fluid circulation path 204 enters cell growth chamber 100 via EC inlet port 128, and leaves cell growth chamber 100 via EC outlet port 132. Media is in contact with the outside of the hollow fibers in the cell growth chamber 100, thereby allowing diffusion of small molecules into and out of the hollow fibers.

Pressure/temperature gauge 224 disposed in the second fluid circulation path 204 allows the pressure and temperature of media to be measured before the media enters the EC space of the cell growth chamber 100. Pressure gauge 226 allows the pressure of media in the second fluid circulation path 204 to be measured after it leaves the cell growth chamber 100. With regard to the EC loop, samples of media can be obtained from sample port 230 during operation. A sample coil 218 such as that found in the IC loop may also be found in the EC loop to remove samples of EC media.

After leaving EC outlet port 132 of cell growth chamber 100, fluid in second fluid circulation path 204 passes through EC circulation pump 228 to oxygenator 232. Second fluid flow path 222 is fluidly associated with oxygenator 232 via oxygenator inlet port 234 and oxygenator outlet port 236. In operation, fluid media flows into oxygenator 232 via oxygenator inlet port 234, and exits oxygenator 232 via oxygenator outlet port 236. Oxygenator 232 adds oxygen to and removes bubbles from media in the CES. In various embodiments, media in second fluid circulation path 204 is in equilibrium with gas entering oxygenator 232. The oxygenator 232 can be any appropriately sized oxygenator known in the art. Air or gas flows into oxygenator 232 via filter 238 and out of oxygenator 232 through filter 240. Filters 238 and 240 reduce or prevent contamination of oxygenator 232 and associated media.

In the configuration depicted for CES 200, fluid media in first fluid circulation path 202 and second fluid circulation path 204 flows through cell growth chamber 100 in the same direction (a co-current configuration). Those of skill in the art will recognize that CES 200 can also be configured to flow fluid in a counter-current conformation. Those of skill in the art will also recognize that the respective inlet and outlet ports can be disposed in the cell growth chamber at any location.

In accordance with at least one embodiment, cells and fluid media can be introduced to fluid circulation path 202 via first fluid inlet path 242. Fluid container 244 (e.g., Reagent) and fluid container 246 (e.g., IC Media) are fluidly associated with first fluid inlet path 242 via valves 248 and 250, respectively. For purposes of priming the various inlet paths, first and second sterile sealable input priming paths 208 and 209 are provided. Cells and fluid proceed through heat exchanger 252 (if used), IC inlet pump 254, and into air removal chamber 256. Air removal chamber 256 is fluidly associated with first circulation path 202. The air removal chamber 256 may include one or more ultrasonic sensors to detect air or the lack of fluid at certain measuring positions within the air removal chamber 256. For example, ultrasonic sensors may be used near the bottom and/or near the top of the air removal chamber 256 to detect air or fluid at these locations. Air or gas purged from the CES 200 during portions of the priming sequence can vent to the atmosphere out air valve 260 via line 258 that is fluidly associated with air removal chamber 256.

Fluid container 262 (e.g., Cell Inlet Bag (or Saline Priming Fluid)) is fluidly associated with the first fluid circulation path 202 via valve 264. Additional fluid can be added to first or second fluid circulation paths 202 and 204 from fluid container 266 (e.g., Wash Solution) and fluid container 268 (e.g., EC Media). Fluid container 266 is fluidly associated with valve 270 that is fluidly associated with first fluid circulation path 202 via distribution valve 272 and first fluid inlet path 242. Alternatively, fluid container 266 can be fluidly associated with second fluid inlet path 274 by opening valve 270 and closing distribution valve 272. Likewise, fluid container 268 is fluidly associated with valve 276 that is fluidly associated with first fluid circulation path 202 via first fluid inlet path 242. Alternatively, fluid container 268 is fluidly associated with second fluid inlet path 274 by opening valve 276 and closing valve distribution 272.

In the IC loop, fluid is initially advanced by the IC inlet pump 254. In the EC loop, fluid is initially advanced by the EC inlet pump 278. An air detector 280, such as an ultrasonic sensor, may be associated with the EC inlet path 284.

In at least one embodiment, first and second fluid circulation paths 202 and 204 are connected to waste line 288. When valve 290 is opened, IC media can flow through waste line 288 that leads to the heat exchanger 252 and then to waste bag 286. Likewise, when valve 292 is opened, EC media can flow through waste line 288 that leads to the heat exchanger 252 and then to waste bag 286. The heat exchanger 252 serves to recover heat from the waste line 288 and make such heat available for heating fluids entering via the first or second fluid inlet paths 242 and 274, respectively.

Cells can be harvested via cell harvest path 296. Here, cells from cell growth chamber 100 can be harvested by pumping media containing the cells through cell harvest path 296 and valve 298 to cell harvest bag 299. When harvesting cells, or at other times as may be desired, distribution pump 294 can pump media through a connector path 282 located between the first and second fluid circulation paths 202 and 204.

Various components of the CES can be contained or housed within an incubator (not shown), wherein the incubator maintains cells and media at a desirable temperature.

As will be recognized by those of skill in the art, any number of fluid containers (e.g., media bags) can be fluidly associated with the CES in any combination. It will further be noted that the location of the air removal chamber, or sensors independent of the air removal chamber, can be at any location in the CES before IC inlet port 108.

Figure 5:
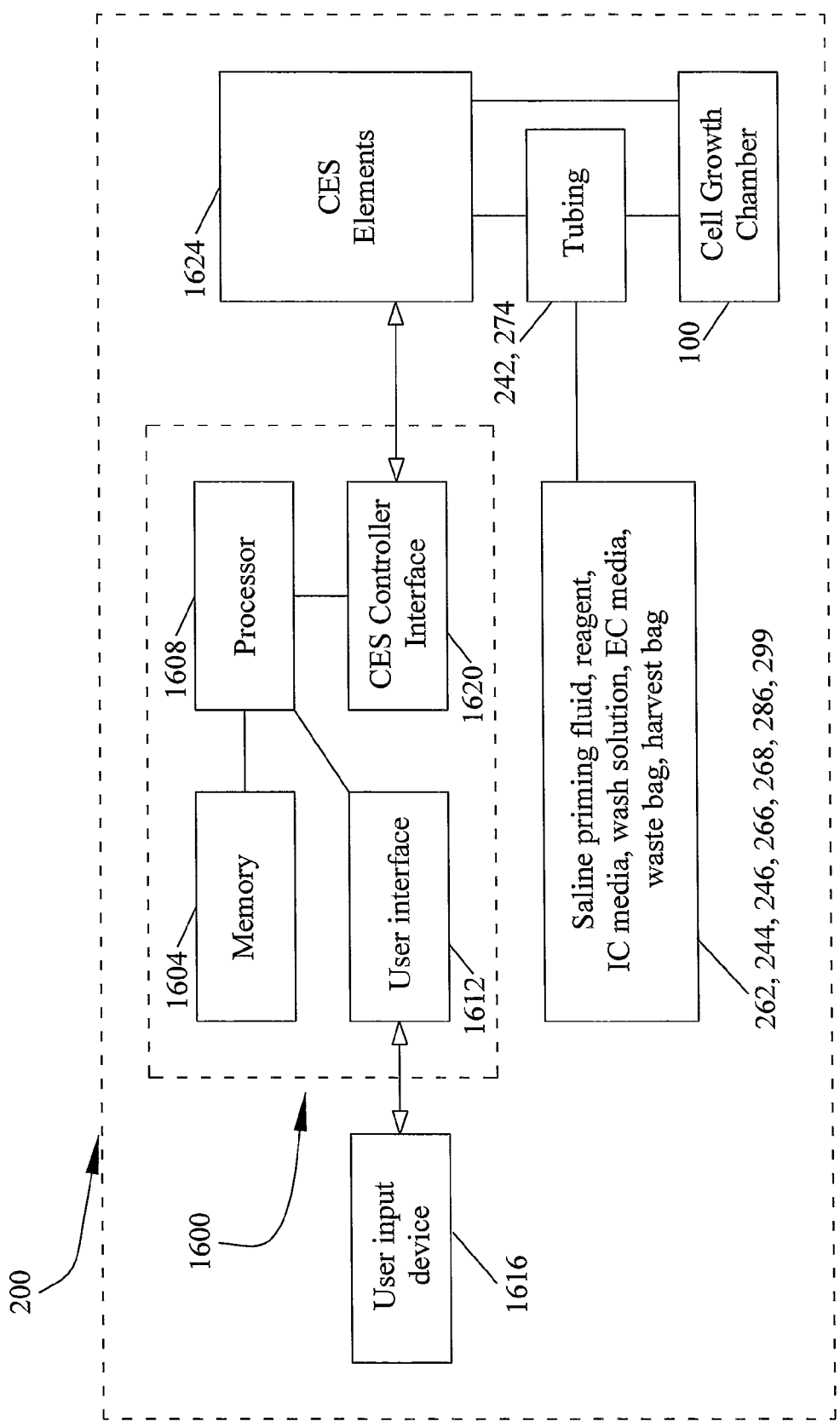
FIG. 5 is a block diagram illustrating a digital computer aspect of the cell expansion system.

As shown in FIG. 5, a digital computer 1600 is operatively associated with the CES 200. The digital computer 1600 includes memory 1604, at least one processor 1608, and a user interface 1612 for receiving instructions from a user via a user input device 1616 (mouse, keyboard, keypad, touch screen, optical sensor or verbal command). In addition, the digital computer 1600 comprises a CES controller interface 1620 for relaying information to and from CES elements 1624 such as sensors pressure, temperature, and biosensor) and for instructing various mechanical systems of the CES 200 such as the pumps and valves. The digital computer 1600 may be in communication with additional sensors for monitoring other aspects of the CES 200, such as whether one or more fluid bags are low and/or empty. Programming utilized by the digital computer 1600 may comprise, by way of example and not limitation, software or firmware.

During an expansion cycle, some amount of fluid is typically removed from the fluid circulation paths (the IC and/or EC circuit) at various times throughout the cell expansion cycle and analyzed for the amount of metabolites and other by-products of cell growth in the fluids. The fluid removed from the fluid flow circuits may be run through any commercially available blood gas analyzer (the blood gas analyzer used in this instance was a Siemens 800 series) to measure the amounts of metabolites contained in the fluid. Using a blood gas analyzer, the concentration of lactate (or glucose) is measured in mM/L. Other methods of measurement such as direct chemistry may also be used.

Metabolites may also be measured using a biosensor. Any commercially available biosensor may be used. If the biosensor is sterile, or is made of a material which may be sterilized with ethylene oxide or gamma irradiation, it may be fluidly connected directly into the fluid lines (in-line). If the biosensor is not able to be sterilized, it may be indirectly connected into the fluid lines via a sterile barrier filter.

Glucose and lactate molecules are small enough that they diffuse equally across the membrane, and are in equilibrium. Therefore, accurate measurements can be taken by any means on either the IC 202 or EC 204 side, or in waste line 288. Fluid may be removed from the IC loop 202 through sampling port 216 or sample coil 218 and/or from the EC loop 204 through sample port 230.

Aerobically growing cells consume glucose and oxygen and produce lactate. The more cells that are present in a cell growth chamber, the more glucose and oxygen are consumed and lactate generated. When cells are at a high density, particularly adherent cells, cell expansion slows due to increased cell-cell interaction between colonies. Cell clumping or aggregation also occurs at high cell density. It is currently not routine practice to look directly inside a cell growth chamber to see if cells are growing into each other without destroying the sterility of the system. Therefore, it would be advantageous if metabolic products of cell growth such as lactate, or products consumed during cell growth such as glucose and oxygen could be used as an indirect measurement to determine if cells were reaching confluence and should be harvested.

An algorithm may be generated to determine the number of cell doublings, which, in turn, determines the best time to reseed or harvest the cells before cell growth slows. The number of doublings can be determined using lactate mass generated and the number of cells initially loaded into the cell expansion system.

Reseeding or harvesting should occur when the number of doublings=d'
N=number of cells in the system
$N_0$=starting number of cells loaded into the cell growth chamber
Rate of change of mass of lactate $m_L$ is proportional to N $$\text{Doubling rate} = \frac{d}{dt}$$

The algorithm is used to determine the number of doubles, which, in turn, determines the best time to reseed or harvest. The number of doubles can be determined from lactate mass $m_L$ and the initial number of cells N in the system.

$$m_L = \frac{d}{dt} \propto N$$

$m_L = g_L N = g_L N_0 (2)^d$ where $g_L$ is generation rate of lactate $(m_L(g))/t(hr)/N$
$N = N_0 (2)^d$ This is the starting number $N_0$ of cells times the doubling rate $(2)^d$ $\ln m_L = \ln g_L + \ln N_0 + d' \ln 2$ for d=d'

$\ln m_L = c + \ln N_0$ where $c = \ln g_L + d' \ln 2$

The log of the lactate mass $m_L$ equals a constant (c)+the log of the starting number ($N_0$) of cells The rate of lactate produced is proportional to the number of cells in the system at any point in time. As increased cell numbers cause decreased cell growth rate, it is expected that lactate generation rate would also decrease. It should also be noted that the numbers that are initially put into the algorithm will change both c and the point at which the line begins to flatten out.

Figure 4:
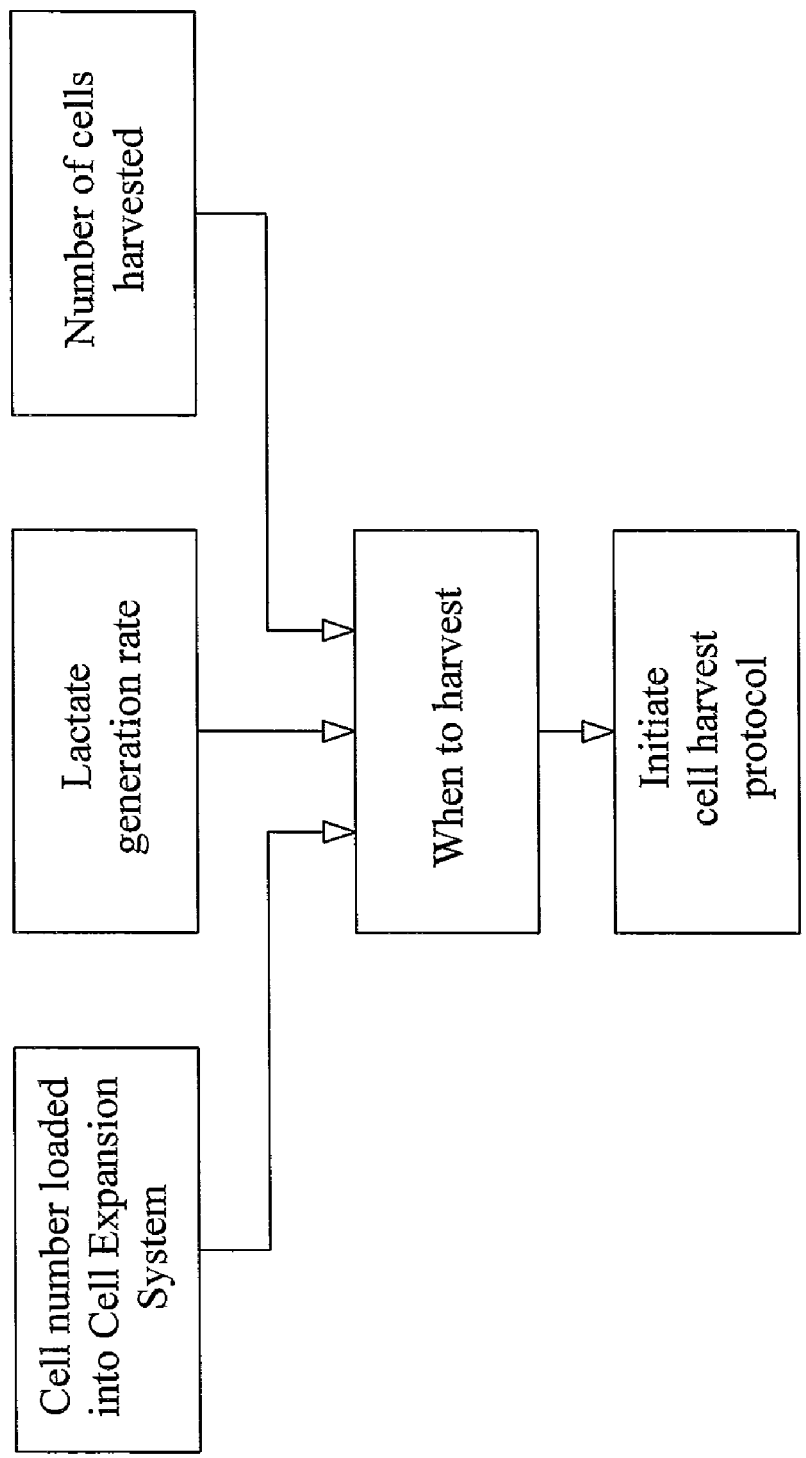
FIG. 4 is a flow chart of the steps of an embodiment of a method for determining when to initiate a harvest procedure.

Using the number of cells initially loaded in the cell growth chamber, the number of cells harvested, and the lactate generation rate at harvest, an algorithm can be generated which can be used to determine when to harvest the cells before cell growth slows and the cells begin to aggregate. This is shown in FIG. 4.

Figure 3:
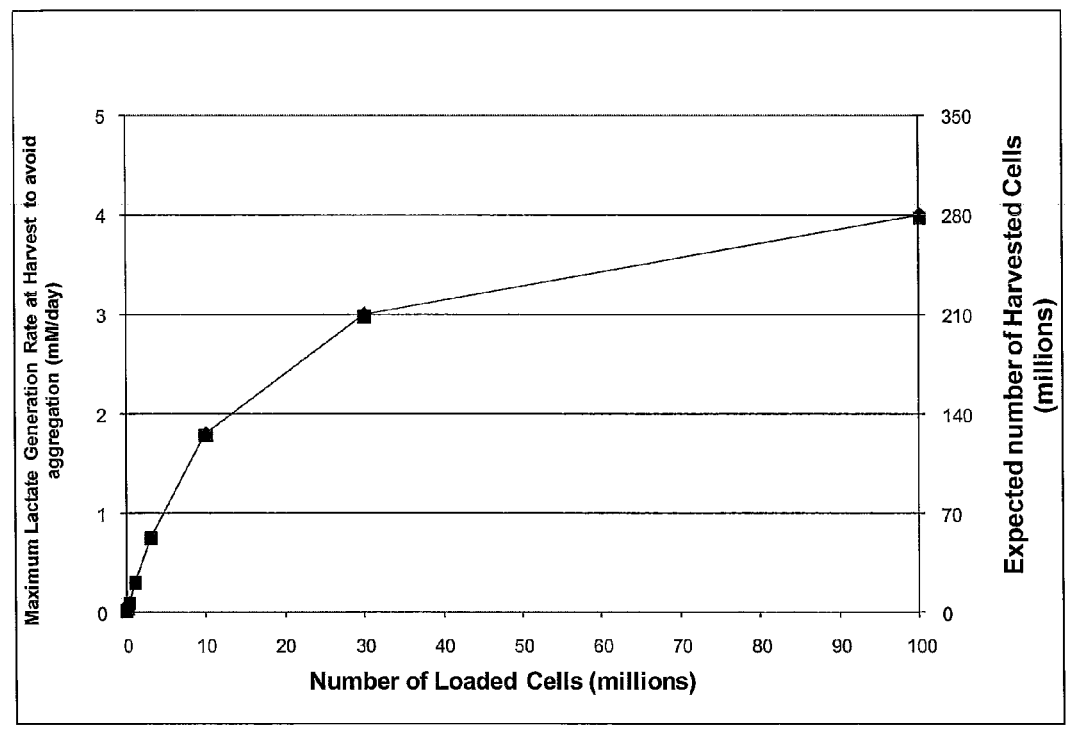
FIG. 3 is a graph depicting when to initiate a harvest procedure.

The algorithm can be depicted graphically as shown in FIG. 3. As would be expected, and as shown from the graph, the curve ceases to be exponential and starts to flatten out when the colonies have gotten large enough to grow into each other.

As but one example, not meant to be limiting, if 10 million cells were initially loaded into a cell growth chamber, and the operator wanted 140 million cells at harvest, the cells should be harvested when the lactate generation rate is around 2.2 mM/day.

The physical manifestation of the algorithm (FIG. 3) can be used by an operator to determine when to harvest cells, or the algorithm can be embedded into a computer program, for use with digital computer 1600.

In at least one embodiment, and as shown in FIG. 4, the digital computer 1600 is connected to a processor having a memory containing the algorithm. During the course of a cell expansion cycle, when a certain amount of lactate has been generated by the expanding cells, the processor will notify the operator that it is time to harvest the cells. In another embodiment, the processor might initiate harvesting protocols when a certain amount of lactate has been generated.

This algorithm can be used to determine when the optimal time to harvest adherent cells is for any type of bioreactor.

It will be apparent to those skilled in the art that various modifications and variations can be made to the structure and methodology of the present invention without departing from the scope or spirit of the invention. Rather, the invention is intended to cover modifications and variations provided they come within the scope of the following claims and their equivalents.

The invention claimed is:

1. A method of determining when to harvest cells from a cell growth chamber of a closed cell expansion system comprising the steps of:
   measuring a number of cells initially loaded into the cell growth chamber;
   removing, through a sampling port, fluid from a fluid circulation path of the closed cell expansion system while maintaining sterility of the closed cell expansion system;
   measuring a concentration of lactate in the fluid; and
   based on the measured number of cells initially loaded and the measured concentration of lactate, determining when to harvest the cells from the cell growth chamber of the closed cell expansion system, wherein the determining comprises:
      executing an algorithm, the algorithm comprising: $\ln m_L = c + \ln N_0$, wherein $m_L$ denotes a lactate mass, $N_0$ denotes the number of cells initially loaded, and c denotes a constant, the constant c comprising: $c = \ln g_L + d' \ln 2$, wherein $g_L$ denotes a generation rate of lactate, and $d'$ denotes a number of cell doublings that will be needed to obtain a desired number of cells to harvest.

2. The method of claim 1, wherein the measuring the concentration of lactate in the fluid also comprises measuring lactate in a waste line of the closed cell expansion system.

3. A computer operatively associated with a closed cell expansion system, the computer comprising:
   a user interface configured to receive:
      a number of cells initially loaded into the closed cell expansion system; and
      a concentration of lactate measured at a first time and at a second time during a cell expansion cycle, wherein the concentration of lactate is measured while maintaining sterility of the closed cell expansion system;
   a memory storing an algorithm to determine when to harvest the cells from the cell growth chamber, the algorithm comprising: $\ln m_L = c + \ln N_0$, wherein $m_L$ denotes a lactate mass, $N_0$ denotes the number of cells initially loaded, and c denotes a constant the constant c comprising: $c = \ln g_L + d' \ln 2$, wherein $g_L$ denotes a generation rate of lactate, and $d'$ denotes a number of cell doublings that will be needed to obtain a desired number of cells to harvest; and
   a processor, in communication with the user interface and the memory, operable to:
      receive the number of cells initially loaded into the cell expansion system;
      receive the concentration of lactate; and
      execute the algorithm at least two times with the number of cells initially loaded and the concentration of lactate at the first time and at the second time to determine when to harvest the cells from the cell growth chamber.

4. A closed cell expansion system comprising:
   a cell growth chamber comprising cells;
   a pump;
   a computer operatively associated with the cell expansion system, the computer comprising:
      a user interface configured to receive:
         a starting number of cells loaded into the cell growth chamber; and
         a concentration of lactate measured at a first time and at a second time during a cell expansion cycle, wherein the concentration of lactate is measured while maintaining sterility of the closed cell expansion system;
      a memory storing an algorithm to determine when to harvest the cells from the cell growth chamber, the algorithm comprising: $\ln m_L = c + \ln N_0$, wherein $m_L$ denotes a lactate mass, $N_0$ denotes the starting number of cells loaded into the cell growth chamber, and c denotes a constant, the constant c comprising: $c = \ln g_L + d' \ln 2$, wherein $g_L$ denotes a generation rate of lactate, and $d'$ denotes a number of cell doublings that will be needed to obtain a desired number of cells to harvest;
      a processor, in communication with the user interface and the memory, operable to:
         receive the starting number of cells loaded into the cell growth chamber;
         receive the concentration of lactate; and
         execute the algorithm at least two times with the starting number of cells loaded into the cell growth chamber and the concentration of lactate at the first time and at the second time to determine when to harvest the cells from the cell growth chamber; and
      a controller interface, in communication with the processor, the controller interface operable to receive a signal from the processor to instruct the pump to pump media through the cell growth chamber to remove the cells from the cell growth chamber.

5. The system of claim 4, wherein the processor is further operable to:
   plot a first result of a first execution of the algorithm on a graph;
   plot a second result of a second execution of the algorithm on the graph;
   plot a third result of a third execution of the algorithm on the graph; and
   predict when to harvest the cells from a curve of the graph, wherein the curve comprises the plots of the first, second, and third results.

6. The system of claim 4, wherein the concentration of lactate is measured while maintaining the sterility of the closed cell expansion system by removing fluid from a fluid circulation path of the system through one or more from the group consisting of: a sampling port and a sample coil.

7. The system of claim 4, wherein the concentration of lactate is measured with a blood gas analyzer.

8. The system of claim 4, wherein the concentration of lactate is measured with a biosensor.

9. The system of claim 8, wherein the biosensor is connected to a fluid line via a sterile barrier filter.

10. The system of claim 4, wherein the controller interface is operable to receive a signal to pump the removed cells to a cell harvest bag.

11. The method of claim 1, further comprising:
   plotting a first result of a first execution of the algorithm on a graph;
   plotting a second result of a second execution of the algorithm on the graph;
   plotting a third result of a third execution of the algorithm on the graph; and predicting when to harvest the cells from a curve of the graph wherein the curve comprises the plots of the first, second, and third results.

12. The method of claim 1, wherein the concentration of lactate is measured with a blood gas analyzer.

13. The method of claim 1, wherein the concentration of lactate is measured with a biosensor.

14. The computer of claim 3, wherein the concentration of lactate is measured while maintaining the sterility of the closed cell expansion system by removing fluid from a fluid circulation path through one or more from the group consisting of: a sampling port and a sample coil.

* * * * *